(12) United States Patent
Rabenecker et al.

(10) Patent No.: US 7,089,778 B2
(45) Date of Patent: Aug. 15, 2006

(54) MODULAR GAS MEASURING SYSTEM

(75) Inventors: Horst Rabenecker, Stockelsdorf (DE);
Thomas Treptow, Rethwisch (DE);
Matthias Martens,
Gross-Schenkenberg (DE); Robert Kessel, Bad Oldesloe (DE); John Cohen, Manchester (GB); Fritz Thiele, Krummesse (DE)

(73) Assignee: Dräger Safety AG & co. KGaA, (DE)

( * ) Notice: Subject to any disclaimer, the term of this patent is extended or adjusted under 35 U.S.C. 154(b) by 11 days.

(21) Appl. No.: 10/839,892

(22) Filed: May 6, 2004

(65) Prior Publication Data
US 2005/0000271 A1  Jan. 6, 2005

(30) Foreign Application Priority Data
Jul. 2, 2003  (DE) ................................. 103 29 834

(51) Int. Cl.
*G01N 27/00*  (2006.01)
(52) U.S. Cl. ....................................................... 73/23.2
(58) Field of Classification Search ................ 73/23.2, 73/29.01, 29.05
See application file for complete search history.

(56) References Cited

U.S. PATENT DOCUMENTS 4,109,509 A * 8/1978 Cramer et al. ............... 73/23.3
5,025,653 A * 6/1991 Schuldt ....................... 73/23.2
5,948,962 A * 9/1999 Matthiessen ................. 73/23.2
6,285,964 B1 * 9/2001 Babel et al. ................ 702/121

FOREIGN PATENT DOCUMENTS

DE    WO 98/47054    * 10/1998
DE    197 55 516 A1    6/1999

OTHER PUBLICATIONS

"How they work | HART Digital Protocol" at http://www.sensorland.com/HowPage045.html.*

* cited by examiner

*Primary Examiner*—Charles Garber
(74) *Attorney, Agent, or Firm*—McGlew & Tuttle, PC

(57) ABSTRACT

A modular gas measuring system with a basic unit (1) with electric supply and data lines connected to it, a measuring unit (2), which is equipped with a gas sensor and with a microprocessor and is connected to the basic unit (1) by means of snap closures to form a functional unit. At least one expansion module, is accommodated by the functional unit. The modular design, of optionally accommodating different expansion modules, so that the properties and the possible applications of the gas measuring system can be expanded in a simple manner.

17 Claims, 1 Drawing Sheet

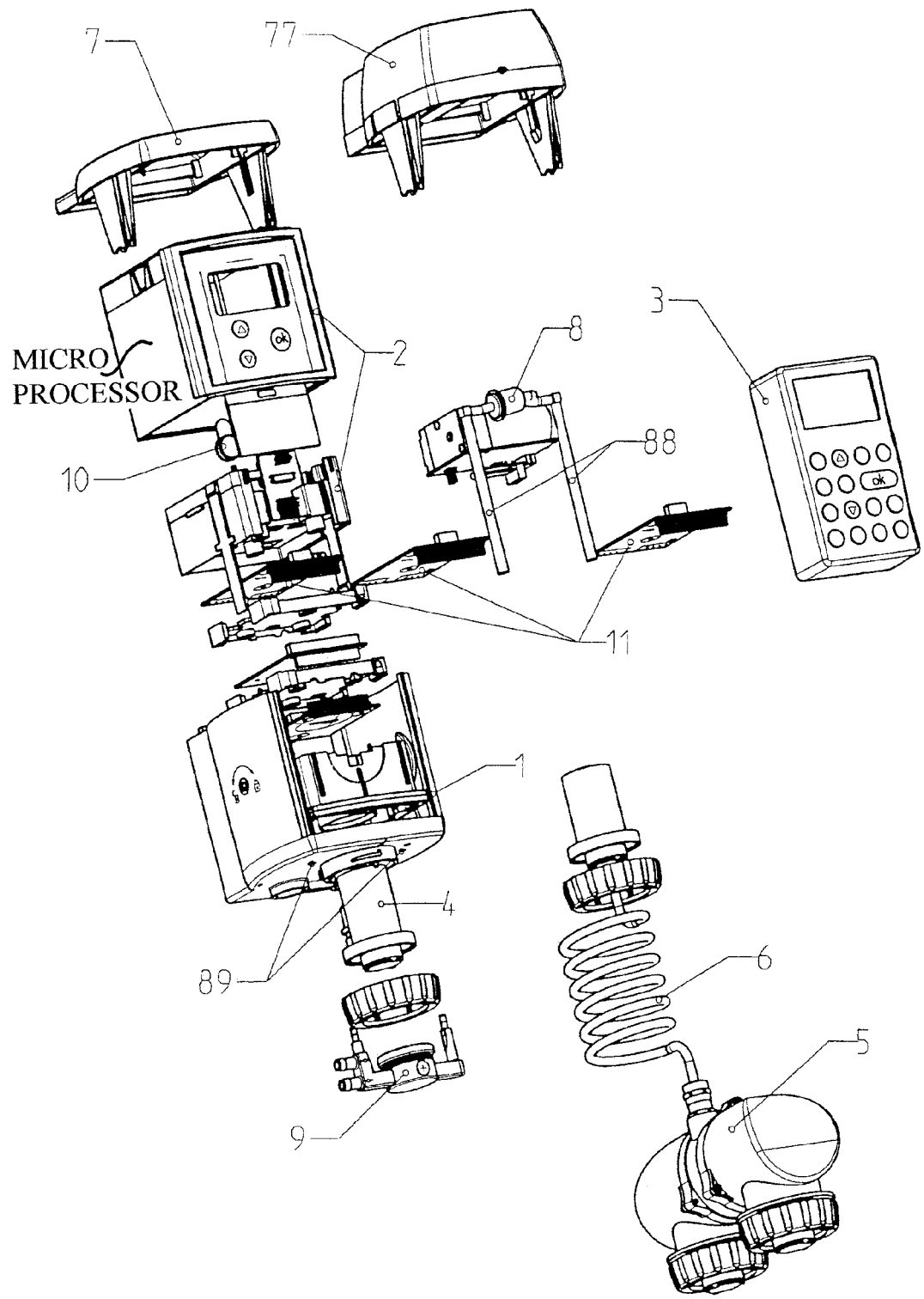

MODULAR GAS MEASURING SYSTEM

CROSS REFERENCE TO RELATED APPLICATIONS

This application claims the benefit of priority under 35 U.S.C. § 119 of German patent application DE 103 29 834 filed Jul. 2, 2003 the entire contents of which are incorporated herein by reference.

FIELD OF THE INVENTION

The present invention pertains to a modular gas measuring system.

BACKGROUND OF THE INVENTION

A prior-art gas measuring system is disclosed in DE 197 55 516 A1. This gas measuring system has a computer unit, which is connected to a sensor circuit for a sensor and is provided with program commands for processing the data measured by the sensor and processed by the sensor circuit. The sensor circuit is associated with a replaceable program module in the computer unit. If another type of sensor is to be used, the sensor with the sensor circuit belonging to it is replaced and the program module is also removed and the program module belonging to the new sensor is loaded into the computer unit.

Stationary gas measuring systems detect gas-specifically different gases or, e.g., an insufficient oxygen concentration by means of different gas sensors and transmit the measured signals to a central unit via a data line.

Different individual technical auxiliary devices for gas measuring systems are known to perform different measurement tasks and to meet special local measurement conditions. For example, a pump with a gas line belonging to it is used to transport gas samples to be measured from inaccessible measuring sites to the gas measuring system. In addition, communication units are known for sending measured data corresponding to the communication standards from a gas measuring system to a central unit or within a gas measuring unit comprising a plurality of gas measuring systems.

SUMMARY OF THE INVENTION

The object of the present invention is to provide a modular gas measuring system that has the possibility of expanding the properties and possible applications of the gas measuring system in a simple manner by the optional inclusion of different modules.

According to the invention, a modular gas measuring system is provided with a basic unit with an electric supply and data lines connected to it. A measuring unit is provided that is equipped with a microprocessor and is connected to the basic unit by means of snap closures to form a functional unit. At least one expansion module is accommodated by the functional unit.

An essential advantage of the gas measuring system according to the invention arises from the modular design with a basic unit with connected supply and data lines, which are installed on the site, and with a measuring unit, which is attached and connected to the basic unit by means of snap closures to form a functional unit. The expansion modules are plugged or snapped into the functional unit when needed and integrated within same, so that only a small installation effort is needed for installation.

An exemplary embodiment of the present invention will be explained on the basis of the only figure, which shows the components of a gas measuring system in a three-dimensional view. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The only FIGURE is a perspective view showing the components of a gas measuring system.

DESCRIPTION OF THE PREFERRED EMBODIMENT

The main components of the modular gas measuring system are the basic unit 1 with mechanical fastening and clamping elements and with electric contact elements for the power supply of the gas measuring system as well as with data lines as well as a measuring unit 2. The measuring unit 2 contains a microprocessor and an internal electronic unit with all functionalities for the evaluation and the processing of the measured signals.

The gas measuring system can be operated via the remote control unit 3 by means of infrared transmission.

The functional unit of the gas measuring system is formed by the basic unit 1 and the measuring unit 2. The functional unit can be expanded by at least one expansion module as follows: Instead of the sensor connection with an especially electrochemical gas sensor 4, a gas sensor module 5 with one or two electrochemical gas sensors with associated sensor electronic units is optionally used, and the electrical connection to the gas measuring system is established via the cable connection 6 and the sensor interface of the measuring unit 2. This interface is designed such that both the analog data of a gas sensor 4 which is plugged directly into the sensor connection and the processed data of the gas sensor module 5 performing the measurement remotely from the measuring unit 2 can be read by the measuring unit 2. The gas sensor module 5 may be operated both with one gas sensor and two gas sensors, which differ, e.g., in terms of the measurement sensitivity or in the measured gas-specific measurement selectivity. The housing of the gas sensor module 5 is designed such that one half of the housing may be optionally omitted if only one gas sensor is used. In the basic outfit, the measuring unit 2 is closed at the top with an attached housing cover 7. In one variant of the gas measuring system, the housing cover 7 is replaced with an expansion module in the form of a relay module 77, which assumes the mechanical function of the housing cover 7, on the one hand, and is additionally used to connect or disconnect external devices, which are connected to the outputs of the relay module 77 and further to the microprocessor and the internal electronic unit of the measuring unit 2 via plugs, as a function of the measured signal of the measuring unit 2. The plugs are preferably arranged protected under an openable flap of the relay module 77. Another expansion module is the pump module 8, which may be installed under the housing cover 7 or the relay module 77. The pump in the pump module 8 is supplied with power directly from the gas measuring system via plug contacts and without additional separate electric power supply. The suction and delivery lines 88 of the pump run within the housing of the gas measuring system and end in two openings 89 to the right and left next to the sensor connection 4. The gas to be measured can be delivered with a plug-in pump adapter 9 to the gas sensor of the measuring unit 2 and then optionally back to the sampling site into an outgoing air line. The pump adapter 9 has a direction of flow that is reversible by plugging it into another socket.

Essential expansion modules are data or program memories that can be simply plugged or snapped into the gas measuring system and can be read by same and are designed either as a key module 10 or as a communication module 11 and assume different functions.

Depending on the preset configuration, key modules 10 release additional software functions already stored in the microprocessor of the measuring unit 2, for example, additional data memory, event memory, preventive maintenance instructions, and expanded measured value displays.

The particular communication module 11 currently being used, which can be replaced in a simple manner, translates the measured data furnished by the gas measuring system into the language of the communication standard used in the entire unit comprising a plurality of gas measuring systems and optionally in a central unit or main unit, for example, into the known standards 4–20 Ma, HART, Profibus, etc. When switching to another communication standard, the communication module 11 currently being used is replaced with the module that is now needed. The changeover is possible with little effort by means of plugs and snaps.

If a gas measuring unit comprises a plurality of gas measuring systems, the communication between the individual gas measuring systems and optionally a central unit may take place, as an alternative, via data lines or via wireless data link, especially radio links or infrared light (radiation).

While specific embodiments of the invention have been shown and described in detail to illustrate the application of the principles of the invention, it will be understood that the invention may be embodied otherwise without departing from such principles.

What is claimed is:

1. A modular gas measuring system comprising:
a basic unit with an electric supply and wireless or wired data lines connected to said basic unit;
a measuring unit equipped with a sensor connection for receiving an electrochemical gas sensor and a microprocessor, and connected to the basic unit by means of snap closures to form a functional unit;
a plurality of expansion modules each adapted to be accommodated by the functional unit at least one of said expansion modules being accommodated by the functional unit and functionally connected to said measuring unit and another of said expansion modules is exchangeable with said at least one of said expansion modules to preform a different function from said at least one of said expansion modules or is accomodated by the functional unit and functionally connected to said measuring unit along with said least one of said expansion modules, said one of said expansion modules being a data or program memory that can be plugged or snapped into the gas measuring system and can be read by the gas measuring system, said another of said expansion modules being a key module or communication module, which can be accommodated in the gas measuring system especially by plugging or snapping in, said key module activating additional evaluation and display functions for the gas measuring system, which are stored in the gas measuring system, said communication module translating the measured signals sent by the gas measuring system corresponding to the communication standard being used, wherein said sensor connection is an interface such that both the analog data of said gas sensor plugged directly into said sensor connection and the processed data of said gas sensor module measuring remotely from said measuring unit can be read by said measuring unit.

2. A modular gas measuring system in accordance with claim 1, wherein another said one of said expansion modules is a relay module used to switch external devices connected to the relay module on and off as a function of the measured signal of the measuring unit.

3. A modular gas measuring system in accordance with claim 1, wherein another said one of said expansion modules is a gas sensor module with a cable connection with an interface between said gas sensor module and the gas measuring system, so that measured signals of said gas sensor module are transmitted to the gas measuring system.

4. A modular gas measuring system in accordance with claim 1, further comprising a central unit and another modular gas measuring system with a basic unit with an electric supply and data lines connected thereto, a measuring unit equipped with a microprocessor and connected to the basic unit by means of snap closures to form a functional unit and an expansion module accommodated by the functional unit wherein the gas measuring systems are connected via data lines or wireless data links to said central unit to form a gas measuring unit.

5. A modular gas measuring system comprising:
a basic unit with an electric supply and data lines connected to said basic unit;
a measuring unit equipped with a sensor connection for receiving an electrochemical gas sensor and a microprocessor and connected to said basic unit by means of snap a quick-acting closures to form a functional unit; and
an expansion module accommodated by said functional unit, wherein said sensor connection is an interface such that both the analog data of said gas sensor plugged directly into said sensor connection and the processed data of said gas sensor module measuring remotely from said measuring unit can be read by said measuring unit, said expansion module being a pump module used to transport gas to be measured via at least one associated gas line formed in part by a pump adapter with reversible direction of flow from or to a gas sensor of the measuring unit.

6. A modular gas measuring system comprising:
a basic unit with an electric supply and data lines connected to said basic unit;
a measuring unit equipped with a sensor connection for receiving an electrochemical gas sensor and a microprocessor and connected to said basic unit by means of snap a quick-acting closures to form a functional unit; and
an expansion module accommodated by said functional unit, wherein said sensor connection is an interface such that both the analog data of said gas sensor plugged directly into said sensor connection and the processed data of said gas sensor module measuring remotely from said measuring unit can be read by said measuring unit;
a central unit with another modular gas measuring system with a basic unit with an electric supply and data lines connected thereto, a measuring unit equipped with a microprocessor and connected to the basic unit by means of snap closures to form a functional unit and an expansion module accommodated by the functional unit wherein the gas measuring systems are connected via data lines or wireless data links to said central unit to form a gas measuring unit.

7. A modular gas measuring system in accordance with claim 6, wherein said expansion module is a relay module, which is used to switch external devices connected to said relay module on and off as a function of the measured signal of the measuring unit.

8. A modular gas measuring system in accordance with claim 6, wherein said expansion module is a gas sensor module with a cable connection with an interface between said gas sensor module and the gas measuring system, so that measured signals of said gas sensor module are transmitted to the gas measuring system.

9. A modular gas measuring system in accordance with claim 6, wherein said expansion module is a data or program memory that can be plugged or snapped into the gas measuring system and can be read by the gas measuring system.

10. A modular gas measuring system in accordance with claim 9, wherein said expansion module is a key module or communication module, which can be accommodated in the gas measuring system especially by plugging or snapping in.

11. A modular gas measuring system in accordance with claim 10, wherein said key module activates additional evaluation and display functions for the gas measuring system, which are stored in the gas measuring system.

12. A modular gas measuring system in accordance with claim 10, wherein the communication module translates the measured signals sent by the gas measuring system corresponding to the communication standard being used.

13. A modular gas measuring system comprising:
a basic unit with an electric supply and, wireless or wired, data lines;
a measuring unit equipped with a microprocessor and connected to the basic unit by means of snap closures to form a functional unit;
a sensor connection mounted on said functional unit;
a first gas sensor connectable to said sensor connection, said first gas sensor measuring gas adjacent to said measuring unit and providing analog data;
a gas sensor module connectable to said sensor connection, said second gas sensor measuring gas remotely to said measuring unit and providing processed data;
said sensor connection including an interface receiving and processing both the analog data of said first gas sensor and the processed data of said second gas sensor module for reading by said measuring unit;
a plurality of expansion modules each adapted to be accommodated by the functional unit.

14. A modular gas measuring system in accordance with claim 13, wherein:
a first of said expansion modules is accommodated by the functional unit and is functionally connected to said measuring unit;
a second of said expansion modules is exchangeable with said first expansion module to preform a different function from said first expansion modules or is accommodated by the functional unit and functionally connected to said measuring unit along with said first expansion module.

15. A modular gas measuring system in accordance with claim 13, wherein:
said one of said expansion modules is a pump module used to transport gas to be measured via at least one associated gas line formed in part by a pump adapter with reversible direction of flow from or to said first gas sensor of the measuring unit.

16. A modular gas measuring system in accordance with claim 13, further comprising:
a central unit and another modular gas measuring system with a basic unit with an electric supply and data lines connected thereto, a measuring unit equipped with a microprocessor and connected to the basic unit by means of snap closures to form a functional unit and an expansion module accommodated by the functional unit wherein the gas measuring systems are connected via data lines or wireless data links to said central unit to form a gas measuring unit.

17. A modular gas measuring system comprising:
a basic unit with an electric supply and wireless or wired data lines connected to said basic unit;
a measuring unit equipped with a sensor connection for receiving an electrochemical gas sensor and a microprocessor and connected to the basic unit by means of snap closures to form a functional unit;
a plurality of expansion modules each adapted to be accommodated by the functional unit at least one of said expansion modules being accommodated by the functional unit and functionally connected to said measuring unit and another of said expansion modules is exchangeable with said at least one of said expansion modules to preform a different function from said at least one of said expansion modules or is accommodated by the functional unit and functionally connected to said measuring unit along with said least one of said expansion modules, said one of said expansion modules is a pump module used to transport gas to be measured via at least one associated gas line formed in part by a pump adapter with reversible direction of flow from or to the gas sensor of the measuring unit, wherein said sensor connection is an interface such that both analog data of said gas sensor plugged directly into said sensor connection and processed data of said gas sensor module measuring remotely from said measuring unit can be read by said measuring unit.

* * * * *